United States Patent [19]

Kauffmann et al.

[11] Patent Number: 5,286,755
[45] Date of Patent: Feb. 15, 1994

[54] COSMETIC COMPOSITION IN THE FORM OF A SOLID GEL

[75] Inventors: Myriam Kauffmann, Lyon; Nathalie Gregoire, Sceaux; Eric Quemin, Villepinte, all of France

[73] Assignee: L'Oreal, Paris, France

[21] Appl. No.: 937,604

[22] Filed: Sep. 2, 1992

[30] Foreign Application Priority Data

Sep. 6, 1991 [FR] France .................. 91 11062

[51] Int. Cl.⁵ .............. A61K 7/02; A61K 7/15; A61K 7/40; A61K 7/48
[52] U.S. Cl. .................. 514/944; 252/89.1; 424/DIG. 5; 424/59; 424/62; 424/63; 424/64; 424/73; 514/557; 514/588; 514/706; 514/844; 514/859
[58] Field of Search ................ 424/DIG. 5; 514/944

[56] References Cited

U.S. PATENT DOCUMENTS 4,840,788  6/1989  Beachell ................ 424/59
4,944,937  7/1990  McCall ................. 424/65

FOREIGN PATENT DOCUMENTS 0260030  3/1988  European Pat. Off. .......... 424/65

OTHER PUBLICATIONS

Search Report of FR 91 11062, May 15, 1992.

Primary Examiner—Dale R. Ore
Attorney, Agent, or Firm—Cushman, Darby & Cushman

[57] ABSTRACT

A solid, transparent or translucent non-alcoholic cosmetic gel contains 65 to 99 weight percent of a polyol, 0.1 to 5 weight percent of a dibenzylidene-ose, 0.1 to 5 weight percent of a hardening agent of the sulfosuccinate type and 0.5 to 40 weight percent of water. The gel is employed in makeup products.

8 Claims, No Drawings

COSMETIC COMPOSITION IN THE FORM OF A SOLID GEL

The present invention relates to a cosmetic composition for application to the skin, the composition being provided in the form of a transparent or translucent solid gel. More particularly, the present invention relates to products for application to the skin in the form of solid cakes or sticks having hydrating properties.

Among cosmetic compositions, provided in the form of transparent sticks, mention can principally be made of deodorants. Their preservation raises a certain number of difficulties for they have a tendency to dry up and to become opaque during storage. In effect, on evaporation of the volatile ingredients, they undergo a contraction phenomenon thereby deforming them and rendering them very friable. Further, on evaporation of the volatile ingredients, they can also become opaque.

Among the volatile ingredients, ethanol is generally employed and its presence can, moreover, cause a drying out sensation on the skin by delipidating and dehydrating it.

The use of a lower alcohol, such as ethanol, is considered necessary so as to dissolve certain of the ingredients and, in particular, the gelling agent such as, for example, dibenzylidene sorbitol.

In this regard reference can be made to U.S. Pat. Nos. 4,154,816 and 4,346,079 as well as European patent application 260,030.

It has now been discovered, in a surprising and unexpected manner, that it is possible to obtain non-alcoholic gels in the form of transparent cakes or sticks by using as the gelling agent a dibenzylidene-ose in combination with a hardening agent of the sulfosuccinate type.

The sulfosuccinates have been described in the literature as constituting surfactant agents having few irritant properties for the skin and hair and having properties that lower the irritant characteristics of anionic surfactants, such as sodium laurylether sulfate.

The present invention thus relates to as a new industrial product, a solid, non-alcoholic cosmetic gel in the form of a cake or stick, this gel containing:

from 65 to 99 weight percent of a polyol,
from 0.1 to 5 weight percent of a dibenzylidene-ose,
from 0.1 to 5 weight percent of a hardening agent of the sulfosuccinate type, and
from 0.5 to 40 weight percent of water.

The use, in accordance with the invention, of a hardening agent of the sulfosuccinate type, in combination with a dibenzylidene-ose provides, by a synergistic effect, rigid non-alcoholic gels.

The solid gels, according to the invention, exhibit none of the prior art disadvantages since they are storage stable, do not become friable, remain transparent and are non-irritating.

The use of a polyol such as, for example, glycerine imparts excellent hydrating properties to the gels.

According to the invention, the polyol is preferably present in an amount ranging from 65 to 80 weight percent and is selected from glycerine, polyglycerine, polyethylene glycols such as compounds of the formula $H\text{-}(OCH_2CH_2)_n\text{-}OH$ wherein n ranges from 6 to 115,000. Among these latter, mention can preferably be made of products known under the CTFA trade names such as PEG-6, PEG-8, PEG-12, PEG-6-32, PEG-20, PEG-150, PEG-7M, PEG-12M and PEG-115M. More particularly preferred are the products sold under the tradenames "Polyethylene glycol 300" and "Polyethylene glycol 20,000" sold by Hoechst, "Polyethylene glycol 400", "Polyethylene glycol 600" and "Polyethylene glycol 1500" sold by BP (British Petroleum), "Carbowax 1000", "Carbowax 8000", "Polyox WSR N-750" and "Polyox coagulant", sold by Union Carbide.

According to the present invention, the polyol can also be propylene glycol, sorbitol or an ether alcohol such as the glycol ethers. Among the latter, mention can particularly be made of the methyl ether of polypropylene glycol (having 2 propyleneoxy groups) and the methyl ether of polyethylene glycol (having 2 ethyleneoxy groups), sold under the tradenames "DOWANOL-DPM" and "DOWANOL DM", by Dow Corning.

These polyols are employed, according to the invention, as a solvent for the dibenzylidene-ose which constitutes the gelling agent.

Representative dibenzylidene-ose compounds usefully employed in the present invention include compounds having the following general formula:

$$\text{(I)}$$

wherein

X and X′, each independently, represent hydrogen, halogen a $C_1$-$C_4$ alkyl, a $C_1$-$C_4$ alkoxy or a carboxyl group, m and n represent a whole number ranging from 0 to 5, and p is 0 or 1.

As representative of the compounds of formula I, mention can principally be made of dibenzylidene sorbitol, dibenzylidene-ribitol and dibenzylidene-xylitol.

These compounds impart rigidity to the composition as well as its transparent or translucent character.

These compounds are known and their preparation has principally been described in European patent application No. 319,917.

The hardening agent of the sulfosuccinate type is preferably present in an amount ranging from 1 to 2 weight percent and is:

either a silicone sulfosuccinate having formula II:

$$\text{(II)}$$

wherein

R represents a divalent radical selected from

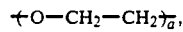 (i)

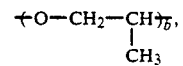 (ii)

and

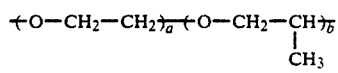 (iii)

wherein a and b range from 0 to 30, x and y are such that the molecular weight ranges from 700 to 1600, and M is an alkali metal such as sodium or potassium, or an ammonium group, or a sulfosuccinate having a sterol chain and having formula (III):

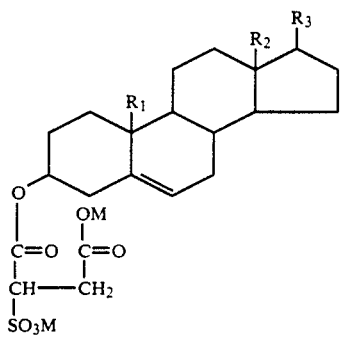 (III)

wherein $R_1$ and $R_2$, each independently, represent hydrogen or —$CH_3$, $R_3$ represents a $C_1$-$C_{20}$ alkyl, and M is an alkali metal such as sodium or potassium or an ammonium group.

Among the silicone sulfosuccinate of formula (II), mention can principally be made of those described in U.S. Pat. No. 4,849,127 the disclosure of which is incorporated herein by reference and in particular the product sold under the tradename "MACKANATE DC 30" by the MacIntyre Chemical Company.

Among the sulfosuccinates having a sterol chain and formula (iii) mention can principally be made of β-sitosterol sulfosuccinate, a compound for which $R_1$ and $R_2$ represent $CH_3$ and $R_3$ is an alkyl having the formula,

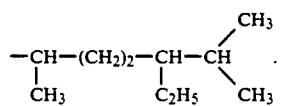

The hardening agents of the sulfosuccinate type, in accordance with formula (II) and (III), have a synergistic effect, in the presence of the dibenzylidene-ose, on the hardness of the product. When they are employed alone, they do not impart any viscosity to the medium which thus remains liquid. On the other hand, when they are added to the dibenzylidene-ose, even in small amounts, they increase the mechanical resistance of the gel by a factor of 2 to 10.

The hardness of the solid cosmetic gel according to the invention is generally between 1.5 and 5 Newton (N).

The cosmetic gel according to the invention can also contain other ingredients to improve its transparency, its cosmetic feel, or which facilitate its manufacture.

Thus, the sticks can include co-solvents for the dibenzylidene-ose, such as butyrolactone, propylene carbonate or pyrrolidone. Humectants such as sorbitol or urea can also be included.

The inclusion of emollient or lubricating oils is facilitated by the presence of the hardening agent of the sulfosuccinate type, the latter imparting, moreover, emulsifying properties to the composition.

Among the oils, mention can be made of mineral oils such as petrolatum oil or isohexadecane, vegetable oils such as apricot or jojoba oil, silicone oils, perfluorinated oils, essential oils and all lipids liquid at the preparation temperature of the solid cosmetic gel.

It is also possible to include foaming agents or surfactant detergents conventionally employed in cosmetics.

Finally, there can be included in the solid gels of the present invention active agents, perfumes, aromatizing agents, preservatives, antioxidants, filters as well as dyes which alter neither the feel nor the transparency of the composition.

There can also be included charges, mineral powders such as talc, silica, titanium oxide, or a metallic oxide as well as any other product conventionally employed in cosmetic and dermo-pharmaceutical compositions. These charges opacify or color the composition and can impart to it certain properties, for example a stratified effect.

Although the invention has been more particularly described with reference to cakes or sticks, it goes without saying that it is also applicable to any other solid form employed in cosmetics, such as for example, pencils having an aqueous appearance.

The active compounds can be of the hydrosoluble, liposoluble or polyol soluble type, for example, vitamins or amino acids, thinning agents for the body and face, such as caffeine and its derivatives, anti-acne agents, antimycosic or antiseptic agents, such as thiolanediol, depigmenting agents such as kojic acid, hydrating agents such as lactic acid or urea or even hyaluronic acid. In a general manner, all the active compounds useful in cosmetic and dermo-pharmaceutical compositions can be included with the reservation, however, that they not be degraded by heat during their production.

The present invention also relates to a process for producing solid sticks or cakes such as defined above.

This process comprises the following steps:

(a) dissolving, in a reactor fitted with a condenser, at a temperature between 130 and 160° C. the dibenzylidene-ose in a polyol, (b) introducing into the reactor a mixture of water and a hardening agent of the sulfosuccinate type, (c) introducing, when appropriate, active compounds and other thermosensitive ingredients, and (d) pouring, into an appropriately shaped mold, the composition and permitting it to cool.

The following non-limiting examples are given to illustrate the invention.

EXAMPLE 1

| Makeup remover composition | weight percent |
| --- | --- |
| Polyethylene glycol 400 | 37 |
| Glycerine | 30 |
| Dibenzylidene sorbitol | 3 |
| "MACKANATE DC 30", 30% aqueous solution of active material, sold by MacIntyre Chemical Company | 5 |
| Decylpolyglucoside, 50% in water, sold under the tradename "APG 300" by Henkel | 10 |
| Propylene glycol alginate | 0.15 |
| Water | 14.85 |

This makeup remover composition can be molded in the form of a transparent cake, which has a hardness of 2N. This cake is very hydrating, foams on application, is easily rinsed off with water and leaves a smooth film on the skin.

EXAMPLE 2

| Shaving "soap" without a soap | weight percent |
| --- | --- |
| Polyethylene glycol 400 | 37 |
| Glycerine | 30 |
| Dibenzylidene sorbitol | 3 |
| "MACKANATE DC 30", sold by the MacIntyre Chemical Company | 10 |
| Polydimethylsiloxane, sold under the tradename "ABIL 10", by Goldschmidt | 1 |
| "APG 300", sold by Henkel | 10 |
| Water | 9 |
| This soap has a hardness of 2.5N. | |

It both foams and lubricates. It is very hydrating and leaves the skin soft.

EXAMPLE 3

| Makeup pencil for the lips | weight percent |
| --- | --- |
| Polyethylene glycol 400 | 37 |
| Glycerine | 32 |
| Urea | 3 |
| Dibenzylidene sorbitol | 4 |
| "MACKANATE DC 30", sold by the MacIntyre Chemical Company | 5 |
| Water | 5 |
| This pencil has a hardness close to 3.5N. | |

It is hydrating and has a good effect for the care of the lips.

EXAMPLE 4

| Hydrating bath cake, without soap | weight percent |
| --- | --- |
| Polyethylene glycol 400 | 37 |
| Glycerine | 30 |
| Dibenzylidene sorbitol | 3 |
| Sodium β-sitosterol sulfosuccinate | 1.5 |
| Water | 28.5 |
| Perfume, sufficient amount | |
| This cake has a hardness of about 3N. | |

EXAMPLE 5

| Thinning stick | weight percent |
| --- | --- |
| Polyethylene glycol 400 | 37 |
| Glycerine | 30 |
| Dibenzylidene sorbitol | 3 |
| "MACKANATE DC 30", sold by the MacIntyre Chemical Company | 5 |
| Water | 19.24 |
| Caffeine | 3 |
| Salicylic acid | 1.26 |
| Triethanolamine | 1.5 |
| The hardness of this stick is about 2N. | |

This stick, applied by massaging, constitutes an excellent thinning composition.

EXAMPLE 6

| Depigmenting stick | weight percent |
| --- | --- |
| Polyethylene glycol 400 | 37 |
| Glycerine | 14 |
| Polyglycerine 500 | 14 |
| Dibenzylidene sorbitol | 4 |
| "MACKANATE DC 30", sold by the MacIntyre Chemical Company | 5 |
| Acetate buffer, pH 4.7 | 24 |
| Kojic acid | 1 |
| This stick has a hardness of about 2.5N. | |

It is easy to apply on the skin and provides good depigmentation of spots.

We claim:

1. A non-alcoholic cosmetic gel in solid form for application to the skin, comprising:
   (i) from 65 to 99 weight percent of a polyol,
   (ii) from 0.1 to 5 weight percent of a dibenzylidene-ose,
   (iii) from 0.1 to 5 weight percent of a hardening agent selected from the group consisting of silicone sulfosuccinate and sterol sulfosuccinate, and
   (iv) from 0.5 to 40 weight percent water.

2. The gel of claim 1 wherein said polyol is present in an amount ranging from 65 to 80 weight percent based on the total weight of said gel.

3. The gel of claim 1 wherein said polyol is selected from the group consisting of glycerine, polyglycerine, a polyethylene glycol, propylene glycol, sorbitol and an ether alcohol.

4. The gel of claim 1 wherein said dibenzylidene-ose has the formula

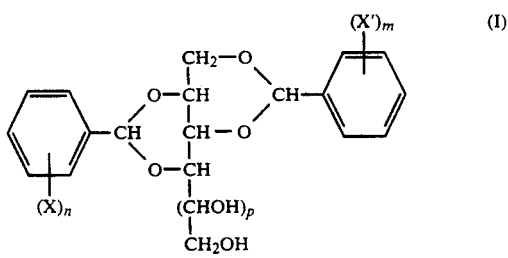

wherein
X and X', each independently, represent hydrogen, halogen, $C_1$-$C_4$ alkyl, $C_1$-$C_4$ alkoxy or a carboxyl group, m and n represent a whole number ranging from 0 to 5, and p is 0 or 1.

5. The gel of claim 1 wherein said dibenzylidene-ose is selected from the group consisting of dibenzylidene sorbitol, dibenzylidene ribitol and dibenzylidene xylitol.

6. The gel of claim 1 wherein said hardening agent is a sterol sulfosuccinate having the formula:

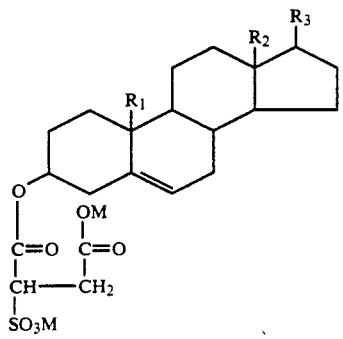

(III)

wherein
$R_1$ and $R_2$, each independently, represent hydrogen or $-CH_3$,
$R_3$ represents a $C_1-C_{20}$ alkyl, and
M is an alkali metal selected from the group consisting of sodium and potassium, or an ammonium group.

7. The gel of claim 1 having a hardness ranging from 2 to 5 Newton.

8. The gel of claim 1 wherein said hardening agent is a silicone sulfosuccinate type having the formula:

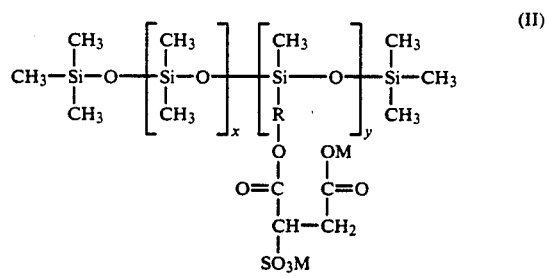

(II)

wherein
R represents a divalent radical selected from the group consisting of:

$$(\text{O}-\text{CH}_2-\text{CH}_2)_a,\quad (i)$$

$$(\text{O}-\text{CH}_2-\text{CH})_b,\quad (ii)$$
$$\qquad\qquad\quad |$$
$$\qquad\qquad\;\text{CH}_3$$

$$(\text{O}-\text{CH}_2-\text{CH}_2)_a(\text{O}-\text{CH}_2-\text{CH})_b,\quad (iii)$$
$$\qquad\qquad\qquad\qquad\qquad\qquad |$$
$$\qquad\qquad\qquad\qquad\qquad\;\text{CH}_3$$

a and b range between 0 and 30,
x and y are such that the molecular weight is between 700 and 1600, and
M is an alkali metal selected from the group consisting of sodium and potassium, or an ammonium group.

* * * * *